United States Patent [19]
Kokernak

[11] Patent Number: 4,583,974
[45] Date of Patent: Apr. 22, 1986

[54] SYRINGE FOR BALLOON DILATION CATHETERS

[76] Inventor: Denis T. Kokernak, 86 Sylvia St., Arlington, Mass. 02174

[21] Appl. No.: 596,546

[22] Filed: Apr. 4, 1984

[51] Int. Cl.[4] ............................................. A61M 5/00
[52] U.S. Cl. .................................... 604/211; 604/99
[58] Field of Search .................................. 604/97-99, 604/207, 208, 211

[56] References Cited

U.S. PATENT DOCUMENTS

| | | |
|---|---|---|
| 361,750 | 4/1887 | Dunbar . |
| 2,475,939 | 7/1949 | Applezweig . |
| 2,702,547 | 2/1955 | Glass . |
| 2,734,504 | 2/1956 | Crescas et al. . |
| 3,155,090 | 11/1964 | Holter et al. . |
| 3,631,847 | 1/1972 | Hobbs, II . |
| 3,993,065 | 11/1976 | Szabo et al. . |
| 4,153,056 | 5/1979 | Silver et al. ........................ 604/211 |
| 4,231,368 | 11/1980 | Becker . |
| 4,270,537 | 6/1981 | Romaine . |
| 4,333,459 | 6/1982 | Becker . |
| 4,370,982 | 2/1983 | Reilly .................................... 604/99 |
| 4,457,712 | 7/1984 | Dragan ................................ 604/211 |

FOREIGN PATENT DOCUMENTS 1006589  4/1957  Fed. Rep. of Germany ...... 604/207

OTHER PUBLICATIONS

"A Simple Mechanical Device for Inflation of Dilating Balloons" by Andrew H. Cragg, M.D. et al., *Radiology*, vol. 147, p. 273, Apr., 1983.
USCI Cardiology and Radiology Products, Division of C. R. Bard, Inc., Box 566, Billerica, MA 01821, U.S.A., 1979 (advertisement).
Medrad, 566 Alpha Drive, Pittsburgh, PA 15238, U.S.A. (advertisement).

*Primary Examiner*—C. Fred Rosenbaum
*Assistant Examiner*—Gene B. Kartchner
*Attorney, Agent, or Firm*—Cesari and McKenna

[57] ABSTRACT

A syringe 10 for use with balloon catheters. The syringe 10 has a pivotable latch 26 which may be selectively engaged with a shaft 20, which drives a plunger 25. The plunger 25 is used to expel and withdraw fluid through an output end port 36. The plunger is moved incrementally with the latch engaged and freely with the latch disengaged.

4 Claims, 4 Drawing Figures

SYRINGE FOR BALLOON DILATION CATHETERS

FIELD OF THE INVENTION

This invention relates to medical instruments and particularly to syringes useful for inflating and deflating balloon catheters inserted into blood vessels or organ ducts.

BACKGROUND

Balloon dilation has been proposed as a procedure to repair stenoses, i.e., partial blockages of blood vessels. These blockages are generally caused by fatty deposits or calcified build-ups on the artery walls. Conventionally, arterial bypass surgery is performed when the blockages or partial blockages restrict arterial blood flow. A relatively recent alternative to bypass surgery is the use of balloon catheters in a procedure known as translumenal angioplasty.

Specifically, translumenal angioplasty is a method in which a balloon catheter is inserted into a partially blocked blood vessel. The catheter is threaded through the vessel to the location of the restriction and then briefly inflated to dilate the vessel permanently and thereby clear the restriction.

Each balloon catheter is designed to inflate to a known diameter, corresponding to the artery in which the procedure is to take place. The catheters are commonly inflated with fluids such as sterile saline solution, since gases should not be used intravascularly and do not give a known balloon displacement.

During angioplasty a catheter with a small balloon tip is passed through the blood vessel and the tip positioned at the restriction site. Correct positioning of the balloon tip at the stenosis site is accomplished through the use of fluoroscopy. The balloon is then inflated by forcing fluid through a connecting catheter tube to the tip. Since the inflated balloon effectively blocks the passage in which it is placed, rapid inflation and deflation are required to prevent the adverse effect of blood flow blockage. Any instrument used to control the balloon catheter should therefore be capable of rapidly inflating and deflating the catheter.

Several instruments relying on relatively complex mechanisms for catheter pressure control are in common use. Some have relatively complex ratchet or clutch arrangements that can be difficult to operate quickly enough under emergency conditions.

A need therefore exists for a simple, easy-to-use medical instrument instrument which allows quick control of balloon catheter inflation and deflation and which can be operated essentially instructively so that a doctor can react immediately to patient condition.

SUMMARY OF THE INVENTION

The invention comprises a syringe having a cylindrical body in which a tubular glass cylinder is enclosed. A moveable plunger within the glass cylinder is attached to a threaded shaft which extends from an end of the syringe. An internally threaded latch member is pivotally attached to the metallic body of the syringe. Pivoting the latch member causes its threads to selectively engage or disengage from the threaded shaft.

When the latch member is engaged with the threaded shaft, rotation of the shaft results in controlled incremental axial movement of the plunger within the glass cylinder. With the latch disengaged, the shaft is free to move axially. A balloon catheter can therefore be partially inflated very quickly with the latch disengaged and then precisely adjusted with the latch engaged to give the pressure required for complete inflation.

It is possible to manipulate the syringe in one hand and easily disengage the latch to quickly deflate the catheter. Further, the instrument's operation is so instinctive that even an unfamiliar operator would be able to react quickly to deflate the catheter.

BRIEF DESCRIPTION OF THE DRAWINGS

FIG. 2 is an expanded view of the base and latch member of the syringe of FIG. 1.

DETAILED DESCRIPTION OF THE INVENTION

Figure 1:
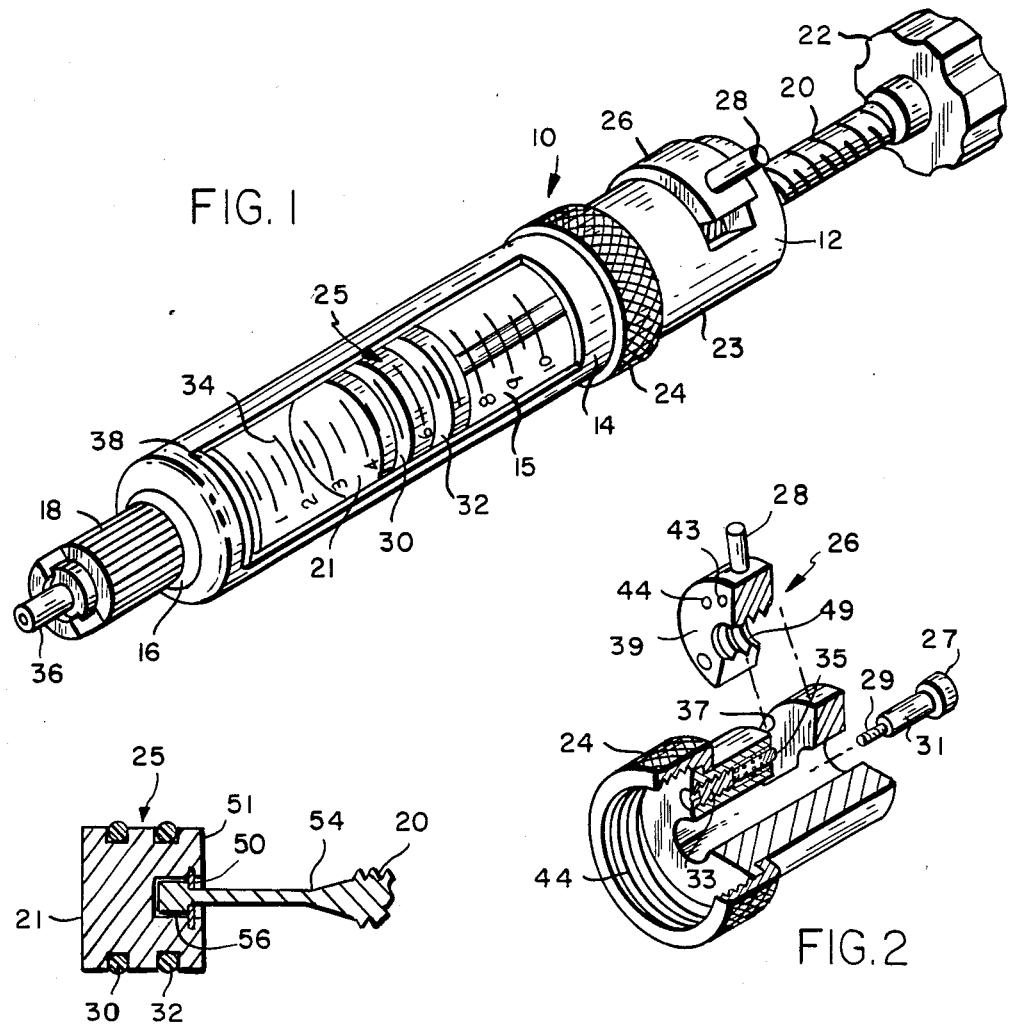
FIG. 1 is a perspective view of a syringe used for the inflation and deflation of balloon catheters.

FIG. 1 is a perspective view of a syringe incorporating the principles of this invention. The syringe 10 comprises a multipiece metallic housing having a base 12, a central barrel 14 and output end 16.

A transparent glass cylinder 15 is positioned within the central barrel 14. The glass cylinder is seated against the base 12 and in turn holds the output end 16 in place in the central barrel. An internally threaded step 44 (FIG. 2) in the base 12 is used to rotatably secure the central barrel 14 to the base.

A moveable plunger 25 is positioned within the glass cylinder 15. The plunger is attached to a threaded shaft 20 so that it can be moved to force fluid out of the syringe's output end 16.

The output end 16 has an end port 36, for fluid entry and exit, which is provided with a conventional luer fitting 18 for attachment to a pressure guage and catheter. The output end is sealed to the glass cylinder by a seal ring 38.

The plunger 25 comprises a metal plug 21 and two recessed seal rings, 30, 32 that provide a fluid seal between the plunger 25 and the glass cylinder. Therefore when the plunger is advanced toward the output end 16, all the fluid between the plunger and the output end is forced out of the end port 36. The glass cylinder 15 is calibrated with lines and numerals 34 which correspond to the volume of fluid in the the glass cylinder. The position of the internal plunger 25 can therefore be correlated with the intake and output of fluid through end port 36 of the output end 16 and thus with the volumetric displacement of a catheter balloon.

Figure 4:
FIG. 4 is a cross sectional view of the shaft and plunger.
Figure 3:
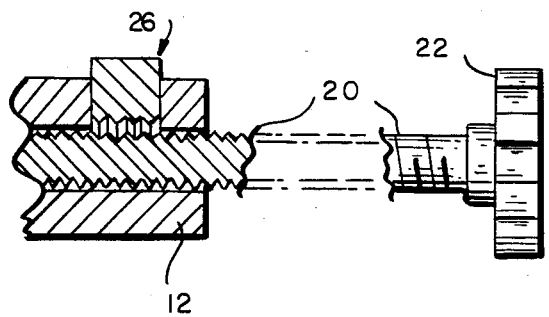
FIG. 3 is a cross sectional view of the base and shaft.

The shaft 20 attached to the plunger 25 is shown in detail in FIGS. 3 and 4. The shaft 20 extends from the plunger 25 through and external to syringe base 12. Near the end of the shaft at the plunger 25, the shaft 20 has a smooth tapered section 54 which terminates in a cylindrical portion 56. The cylindrical portion 56 is held inside the plunger by a snap ring 50, which seats in a goove 51. The snap ring holds the shaft to the plunger so that they move together axially, while allowing free rotation of the shaft relative to the plunger. A knob 22 at the external end of the shaft is used to control plunger position.

The syringe base 12 has a roughened grip 24 and flat section 23 which make it easy to hold the syringe for manipulation. A latch 26 is positioned in the base opposite the flat section 23.

The latch 26 is attached to the base 12 so that it can pivot between engaged and disengaged positions. As shown in FIG. 2, the latch is shaped as a half annulus to match the cylindrical base 12. The latch pivot is formed by recessed machine screw 27, which has a threaded end 29 and a smooth bearing section 31. The latch rotates on the bearing section 31 for easy movement.

Latch 26 is threaded on its inner circumferential surface. These threads 49 match the threads of shaft 20 so that when the latch is closed (FIG. 3) the threaded shaft 20 and plunger 25 may be moved by only rotation of the knob 22 in a screw-type operation of the shaft. When the latch is released, i.e., disengaged, (FIG. 2) the shaft is free to slide axially. The latch is operated through the use of a handle 28.

A conventional spring ball and detent arrangement is used to stabilize and identify latch position. A recessed machine screw locks a locating screw 35 with a sprung ball tip into a slightly elevated position relative to base recess surface 37. The spring ball is thereby positioned against latch surface 39. Latch surface 39 is polished to facilitate smooth movement of the surface against the ball 35 between two set position recesses, or detents, 41 and 43. When the latch is in the closed position, the ball tip is positioned in detent 41; when in open position, the bearing tip is positioned in detent 43.

As stated above, the balloon dilation of stenotic blockages in bodily passages requires that the syringe or mechanism used to inflate and deflate the balloon catheter be both precisely adjusted and be capable of rapid response. Accurate pressurization of balloon catheters is a necessity since over-pressurization can result in bursting of the catheter which can damage arteries and release unwanted substances into the blood stream.

The syringe herein described is extremely simple to operate. The latch mechanism is virtually incapable of jamming or failing to release. The spring ball and detents insure that latch 26 will lodge in the desired position unless intentionally moved. This arrangement avoids accidental partial engagement of the latch which could result in inadvertent syringe release, shaft thread damage, or a failure to force fluid out of the syringe.

When the syringe 10 is attached to a pressure gauge and balloon catheter, the balloon catheter can be quickly and precisely inflated. The pressure gauge (not shown) and the sight glass 15 are used to control the amount of fluid pumped into the catheter and the resulting hydrostatic pressure inside the catheter. With the latch in the open position (as shown on FIG. 1) knob 22 can be moved axially until an approximate, but lower than ultimately desired pressure value is read on the gauge. The latch is then closed and knob 22 is rotated to trim the catheter to the exact pressure desired. The pressure gauge is used to precisely set the pressure in the balloon catheter. The graduated numbers 34 may be helpful to determine the degree of catheter inflation in large arteries. Rotation of the shaft with the latch closed provides sufficient mechanical advantage to easily set the desired catheter pressure.

After the blood vessel is properly dilated, pressure is quickly removed and the catheter deflated by flicking open latch 26 and allowing the plunger to move towards the base 12 to relieve the hydrostatic pressure. The pressure within the glass cylinder 15 and the catheter is generally sufficient to cause automatic axial retraction of the plunger when the latch 26 is released. This retraction of the plunger automatically releases catheter pressure. Suction is easily provided through further axial retraction of the plunger with the latch disengaged. The suction provides a modest vacuum in the catheter which can be maintained by engaging the latch. Vacuum deflation of the catheter allows for its easy withdrawal from the blood vessel.

Devices used in the operating room environment must be easy to understand and manipulate in order that delays and mistakes can be avoided. The syringe 10 is constructed so that it can be easily manipulated with one hand and latch 26 instinctively released with the flip of a finger. Latch 26 thereby permits virtually foolproof inflation and deflation of balloon catheters.

Another important feature of the balloon catheter inflation syringe 10 is that it can readily be constructed of materials that are capable of withstanding both high temperature autoclave sterilization and ethylene oxide gas sterilization. This is important since the device must be sterilized before each use. If it were not capable of withstanding both of these two common sterilization techniques, accidental use of an incorrect sterilization technique could cause imperceptible damage it might result in failure during a critical use.

While the invention has been particularly shown and described with the references to the preferred embodiment thereof, it will be understood by those skilled in the art that various changes and form and detail may be made therein without departing from either the spirit or scope of the invention as defined by the appended claims.

I claim:

1. A syringe for use with a ballon catheter, said syringe comprising:
    a housing containing a cylindrical chamber;
    a plunger enclosed within said cylindrical chamber;
    said housing having an output junction for fluid connection to said balloon catheter;
    a threaded shaft attached to said plunger and extending axially from said housing;
    a pivotable internally threaded latch which is mounted on said housing and thereby fixed against axial movement with respect to said housing and which can be selectively engaged with said threaded shaft for incremental movement of the plunger and disengaged from said threaded shaft for rapid axial movement of said plunger and shaft.

2. The syringe of claim 1 further comprising a spring ball positioned in said housing and adjacent to said latch wherein said latch has detents which act cooperatively with the ball to stabilize the latch positions selected.

3. The syringe of claim 1 wherein the latch further comprises a handle for easy manipulation.

4. A syringe for pressurization and depressurization of a balloon catheter comprising:
    a generally cylindrical, multipieced body comprising a base, a center cylinder, and a narrowed output end;
    a transparent tube enclosed within said center cylinder;
    a plunger positioned within said tube for axial movement within said tube;
    a threaded shaft attached to said plunger and extending outside of said multipieced body at said base;
    said base including a latch section surrounding said shaft, said latch section including an internally threaded latch member pivotably attached to said base for selective engagement with said shaft and a cooperating nonthreaded portion diametrically opposed to said threaded latch member, thereby permitting sliding movement of said shaft over said cooperating portion.

* * * * *